United States Patent [19]
Singer

[11] Patent Number: 6,077,711
[45] Date of Patent: Jun. 20, 2000

[54] FRANGIBLE AMPULE SPECIMEN TEST CARD

[76] Inventor: Jason Singer, 2331 N. Southport, Chicago, Ill. 60614

[21] Appl. No.: 09/030,174

[22] Filed: Feb. 25, 1998

[51] Int. Cl.[7] .................................................. G01N 33/72
[52] U.S. Cl. ........................... 436/66; 436/164; 436/165; 436/169; 422/55; 422/56; 422/58
[58] Field of Search .................................. 422/55, 56, 58; 436/66, 164, 165, 169

[56] References Cited

U.S. PATENT DOCUMENTS

| | | |
|---|---|---|
| 3,689,224 | 9/1972 | Agnew et al. . |
| 4,329,317 | 5/1982 | Detweiler et al. . |
| 4,365,970 | 12/1982 | Lawrence et al. . |
| 4,382,064 | 5/1983 | Detweiler et al. . |
| 4,562,043 | 12/1985 | Mennen et al. . |
| 4,647,541 | 3/1987 | Guadagno et al. . |
| 4,789,629 | 12/1988 | Baker et al. . |
| 4,857,453 | 8/1989 | Ullman et al. . |
| 4,965,047 | 10/1990 | Hammond . |
| 5,100,619 | 3/1992 | Baker et al. . |
| 5,119,830 | 6/1992 | Davis . |
| 5,264,181 | 11/1993 | Schreiber . |
| 5,328,664 | 7/1994 | Ponsy . |

*Primary Examiner*—Terrence R. Till
*Assistant Examiner*—Jennifer McNeil
*Attorney, Agent, or Firm*—Hovey, Williams, Timmons & Collins

[57] ABSTRACT

A method and apparatus for testing tissue samples is provided which includes an integrated specimen test card. The test card is especially useful in testing for the presence of blood in stool samples and includes a frangible ampule contained within a channel mounted on the test card, the ampule containing a developer and the test slide being impregnated with a chromatographic reagent. Upon crushing the ampule within the channel, the developer is directed along a canal to a test section of the slide where, upon diffusion of the developer through the slide and moistening of the test slide by the developer in the presence of blood, a chromatographic reaction occurs to indicate to the user the presence of blood. A discrete control section having a second slide impregnated with reagent and a control indicator, such as hemoglobin, may be provided so that developing liquid can be directed simultaneously both to the test section of the slide and the control section of the slide.

35 Claims, 1 Drawing Sheet

FRANGIBLE AMPULE SPECIMEN TEST CARD

BACKGROUND OF THE INVENTION

1. Field of the Invention

This invention relates to a test medium for medical specimens such as stools which is self-contained including the developer for permitting single use without the need for additional articles for administering the developer. More particularly, it is concerned with a test card which includes a frangible ampule containing a developer and located within a channel. Upon the application of pressure to break the ampule, the developer flows within the channel and is directed to a specimen receiving surface or slide having a reagent thereon for permitting quick and easy handling and testing of the specimen.

2. Description of the Prior Art

In the field of medical diagnostics, it is desirable to obtain rapid test results, preferably on-site without the need for referring the sample to a laboratory. Such tests are known in the medical arts, for example, in occult blood test slide cards for determining the presence of blood in feces, also known as the stool. One existing test card for determining the presence of blood in the stool is sold by SmithKline Diagnostics, Inc. under the trademark Hemoccult, and further illustrated and described in U.S. Pat. No. 4,365,970, with specific slides and their compositions further described in U.S. Pat. Nos. 4,329,317 and 4,382,064 incorporated herein by reference.

The aforementioned test card employs a pivotal cover over the reagent carrying test slide which is beneficial, but requires separate handling of a bottle containing the developing solution to be applied to the slide with the specimen received thereon. As a result, a separate bottle of developing solution is required for use with the test card. This produces problems in that the developing solution is frequently misplaced, the additional time required to use the bottle, and the fact that the feces smeared card must be manipulated and the flap controlled, all while unscrewing the bottle cover and applying the developing solution. In addition, the control region of the card is remotely located from the specimen-receiving test slide such that further applications of the developer are required to a separate area. As a result of the need to handle the separate bottle, the application of the developer to the control region may be infrequent. An improved test card is needed which provides both a control and a test slide but which avoids the problems set forth above.

SUMMARY OF THE INVENTION

These and other objects are largely met by the frangible ampule specimen test card of the present invention. That is to say, the test card as shown and described herein permits the user to apply the sample to the test slide of the card and direct a flow of developer from a frangible ampule carried on the card through channels leading to the slide. Moreover, the frangible specimen test card hereof permits the developer to flow both to the slide carrying the specimen as well as to a control slide without the necessity for carrying a separate bottle which requires manipulation and may be misplaced. Beneficially, the preferred embodiment of the test slide hereof is configured to inhibit application of the specimen to the control region and to thereby enhance proper usage.

Broadly speaking, the frangible specimen test card hereof includes a carrier carrying a specimen-receiving test slide onto which a medical specimen is placed for testing, a frangible ampule containing a quantity of developer, and a channel for directing a flow of the developer directly to the test slide. A separate control slide impregnated with a chromatographic reagent may be provided, with either a separate frangible ampule and channel fluidically communicating with the control sample or, alternatively, the same frangible ampule being provided with a channel system which divides the flow of developer and directs it to both the sample slide and the control slide. The slides are made of material which is fluid permeable and the developer comes into contact with substantially all of each slide through capillary action or direct fluid flow or a combination thereof. The slides are separated by the carrier which is of cardboard, synthetic resin or less permeable material and which is sufficiently resistant to fluid flow to provide independent test results of the sample and control slides and act as a barrier therebetween. In preferred embodiments, the carrier is glued together between center and back panels, the glue acting as a barrier to flow of the developer between the test slide and the control slide.

In a first alternate embodiment, the channel may be divided into two canals each provided with check valves for inhibiting backflow of any developer from one slide to another. In another embodiment where two separate frangible ampules are provided, a rigid member may be placed in spanning relationship over channels containing the two frangible ampules whereby the user may press the member to break both ampules simultaneously.

Other advantages and details of the invention will be readily appreciated by those skilled in the art with reference to the drawings and the detailed description thereof.

DESCRIPTION OF THE PREFERRED EMBODIMENT

Figure 1:
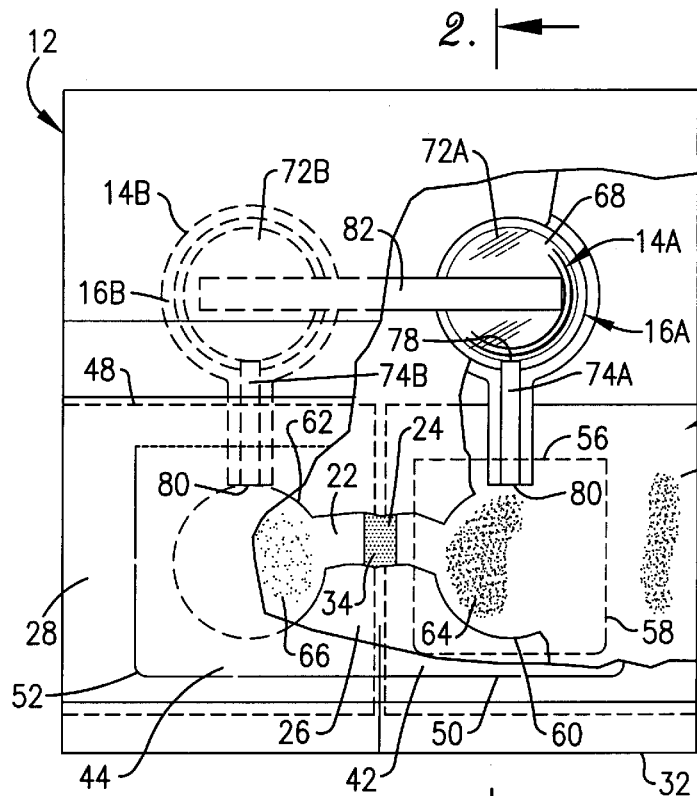
FIG. 1 is a plan view of a first embodiment of the frangible ampule specimen test card hereof, with a one ampule, channel and a portion of one slide shown in phantom and portions of the carrier and front hinged flap broken away for clarity to show the test slide and the rear flap in phantom.
Figure 2:
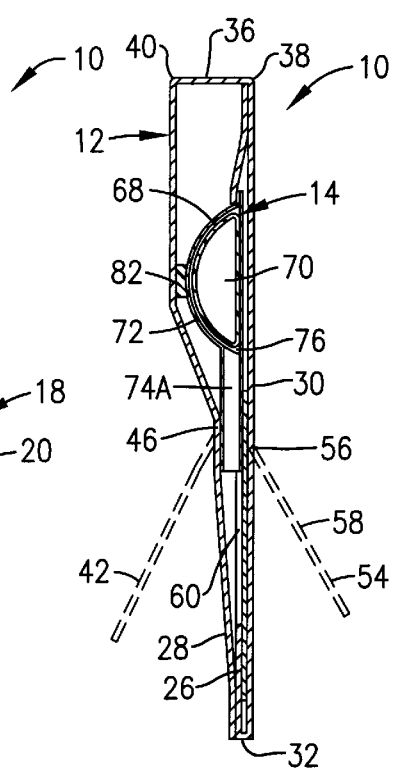
FIG. 2 is a side elevational view thereof showing the hinged flaps over the front and rear portions of the carrier lifted for access to the front of the slides and the rear portion of the test slide.

Referring now to the drawing, a frangible ampule specimen test card 10 is shown in FIGS. 1 and 2 and broadly includes a carrier 12, a frangible ampule 14, a channel 16, and at least one slide 18 for receiving a specimen such as a stool specimen thereon. The test card 10 as described herein is particularly useful in determining the presence of occult blood in a stool specimen. Advantageously, the slide 18 may be divided into a segregated first slide section 20 for receiving a tissue specimen to be tested and second slide section 22 which may be impregnated with a chromatographic reagent for serving as a control to verify the developer within the ampule is operative, with a barrier 24 provided between the first and second slide sections to inhibit any communication of fluid therebetween. Also, as shown in U.S. Pat. No. 4,365,970, incorporated herein by reference, separate positive and negative control areas may be defined by an additional tab (shown as reference character "34" in the U.S. Pat. No. 4,365,970 ) presenting two holes therein for receiving developer applied thereon for providing a control of either a positive or negative result.

In greater detail, the carrier 12 may be formed of thin cardboard or other protective and substantially non-permeable material such as synthetic resin and preferably, presents a center web 26, a front side 28 and a back side 30. The back side 30 is shown connected to the center web 26 by a bottom fold 32 and also by a line of glue 34 which serves both as barrier 24 and also retains the first slide section 20 and second slide section 22 in position. Other relatively impermeable materials may be used as barrier 24, or one of the center web 26 or back side 30 could include an extension which divides the first and second slide sections. The front side 28 is joined to back side 30 by panel 36 along back fold 38 and front fold 40, and further may be glued or otherwise secured such as by a staple along the bottom edge of the front side 28.

The front side 28 includes a pair of front flaps 42 and 44 positioned over the first slide section 20 and the second slide section 22 respectively, each of the flaps 42 and 44 being pivotally carried by respective front hinges 46 and 48. It may be understood that a single front flap extending over both the first and second slide sections may be provided instead of separate flaps. The other boundaries of the front flaps 42 and 44 other than the hinges are defined by U-shaped front flap margins 50 and 52 which may be either a line of weakening such as perforations, a line of separation formed by die cutting, or by a free margin when the front flaps 42 and 44 extend downwardly co-extensive with the remainder of the front side 28 as viewed in FIG. 1.

Similarly, the back side 30 includes a back flap 54 pivotally carried along back hinge 56, with the other boundaries of the back flap 54 being defined by a U-shaped back flap margin 58, which also may be a line of weakening, a line of separation, or a free margin. Preferably, the front side 28 extends over the frangible ampule 14 as illustrated in FIG. 2, so that the channel 16 is beneath and extends beyond both the front hinges 46 and 48 and the back hinge 56. Further, the back flap 54 is positioned over and thus preferably opens to reveal only the first slide section 20, thereby inhibiting confusion which might be caused by application of the stool or other specimen to the control or second slide section 22.

The center web 26 is cut or formed to present at least one and preferably two or more web openings 60 and 62 defining therewithin the first slide viewing section 64 for viewing the test results when the developer is applied to the first slide section 20 and the second slide viewing section 66 for viewing the results of the application of the developer to the control or second slide section 22. The front flaps 42 and 44 and the back flap 54 are positioned in covering relationship to the first slide test section 20 and the second slide test section 22 so that a either front flap 42 or 44 may be pivoted along its respective hinge to expose either the first slide viewing section 64 or the second slide viewing section 66, but only access to the back side of the first slide section is permitted for applying a tissue specimen such as a stool smear thereto. This arrangement permits both the first and second slide sections 20 and 22 to be selectively exposed for viewing of the test results once the ampule is crushed, but only the test slide, i.e. the first slide section 20 to be accessible from the back for application thereon of the tissue, stool or other sample, while the ampule 14 remains covered. Only the viewing sections 64 and 66 are exposed when either of the front flaps 42 and 44 are lifted, or a slightly larger area of the first test slide 20 when the back flap 54 is lifted. The panel 36 presents a depth for receiving the ampule 14 and channel 16 between the front side and the back side.

The ampule 14 includes a body 68 provided of a transparent frangible material such as glass or rigid synthetic resin material. As shown in the drawings, the body 68 of the ampule 14 is in the shape of an oblate or flattened hemisphere although other shapes could also be used. The ampule 14 also includes a developer 70 enclosed within the body 68. The specific developer 70 used will depend on the type of test to be conducted, but by way of example, a stabilized aqueous solution of less than 5% hydrogen peroxide in 75% ethanol is useful in connection with testing for the presence of blood in stool samples. The volume of developer 70 contained within the ampule 14 is sufficient to flow through the channel and communicate with the first and second slide sections, with volumes of less than 1 ml typically being sufficient as only a drop or two of the developer must communicate with the slide 18 which acts through capillary action to deliver the developer thereacross. In the embodiment shown in FIG. 1, two ampules 14A and 14B are provided, while in the embodiment shown in FIGS. 3 and 4, a single ampule 14 communicates with separate slide sections 20 and 22 through the bifurcated channel.

The ampule 14 is contained within the channel 16 which is transparent and preferably of a resilient synthetic resin material resistant to breakage, such as high density polyethylene. The channel 16 is mounted by gluing or mechanical attachment to the center web 26 and includes a blister 72 for receiving the ampule 14 and at least one canal 74 in fluidic communication with the interior 76 of the blister 72 and leading to slide 18. The blister 72 is substantially greater in volume than a canal 74 buy only relatively slightly greater in volume than the body 68, such that the tubular canal 74 retains only a small fraction of any developer displaced when the blister 72 is compressed to crush and fracture of the ampule 14. The canal 74 presents a proximate open end 78 communicating with the interior 76 of the blister but not into ampule 14, and a remote open end 80 adjacent slide 18. In the first embodiment shown in FIGS. 1 and 2, each ampule 14A and 14B are resident within respective separate blisters 72A and 72B of segregated channels 16A and 16B, each channel having its own respective canal 74A and 74B for communicating the developer to separate first and second slide sections 20 and 22. The blisters 72A and 72B may be operatively connected by a rigid press bar 82 overlying each blister in spanning relationship.

Figure 3:
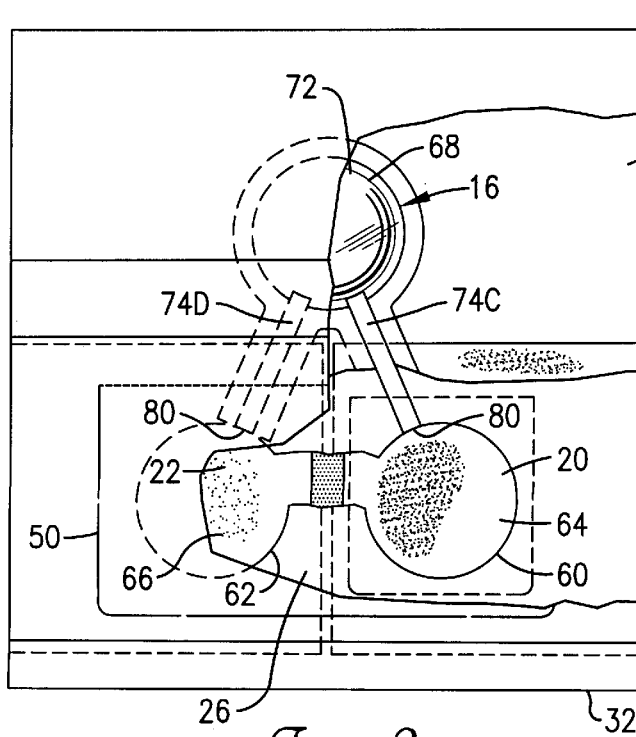
FIG. 3 is a plan view of an alternate embodiment of the frangible specimen test card hereof with a portion of the carrier broken away, showing the use of a single frangible ampule contained within the channel and two separate canals leading to two different slides.
Figure 4:
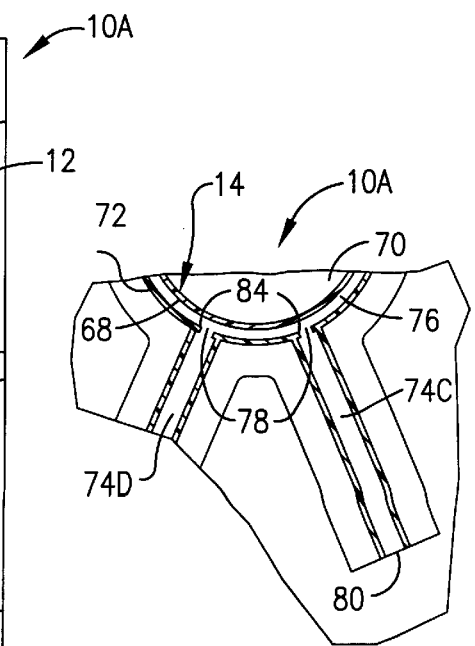
FIG. 4 is an enlarged cross-sectional view of the frangible ampule and channel shown in FIG. 3, showing the use of check valves to restrict the flow of developer to inhibit backflow from one canal to the other.

In the second embodiment of the test card 10A shown in FIGS. 3 and 4, the channel 16 has a single blister 72 communicating with two separate canals 74C and 74D each leading to separate first and second slide sections 20 and 22. Further, each of the canals 74C and 74D may be provided with a check valve 84 positioned at the proximate open end 78, as shown in FIG. 4. The check valve 84 need not be sophisticated, but may merely be a restriction in the diameter of the canal 74 whereby the flow of developer under pressure from the channel to the slide is able to flow therepast, whereas after expression from the blister 72 and removal of pressure, the restriction serves as a check valve sufficient to inhibit backflow of unpressurized developer back into the blister or eventual passage from one canal to another.

The slide 18 is preferably presented in separate first and second slide sections 20 and 22, and the carrier 12 may additionally carry separate control sections. In the case of test slides for measuring the presence of blood in the stool, the slide sections 20 and 22 may be of the same or separate sheets of thin permeable and absorbent tissue paper impregnated with a chromatographic reagent. One acceptable reagent for such uses is guaiac. When a control area is desired, the second slide section 22 may be provided as a positive control section impregnated with a substance which reacts with guaiac when the developer is applied, e.g., hemoglobin. A remote negative control section which is isolated from the test and positive control sections of the slide may be positioned remotely on the carrier and receive no guaiac-reactive substance thereon. Additional canals 74 may be provided to fluidically connect the blister to separate positive and negative control areas.

In order to use the frangible ampule specimen test card 10 of the present invention, the user need only lift the back flap 54 of the carrier 12 and smear a specimen, such as a stool specimen, onto the back side of the first slide section 20. The user then lifts the front flaps 42 and 44 and presses on the blister 72 to fracture the ampule 14, causing developer 70 to be placed under pressure and flow into the interior of the blister 72 and the remainder of the channel 16. The applied pressure reduces the volume of the blister 72 sufficiently to cause the developer to flow into the canal or canals to the test section, e.g. first slide section 20 on the front side thereof opposite the smeared specimen. In the case of the first embodiment shown in FIGS. 1 and 2, the application of pressure to the press bar (82) serves to collapse the blister and fracture the ampule in each channel 16A and 16B. In the second embodiment shown in FIGS. 3 and 4, the pressure applied by the users thumb to the single blister is sufficient to direct the flow of developer past the check valves of the respective canals 74C and 74D and then to the first and second sections 20 and 22. In both embodiments, the first slide section 20, being preferably white and impregnated with guaiac, then turns blue when the developer 70 diffuses through the first slide 18 and moistens that portion of the slide 18 in contact with the stool specimen if blood is present, but does not change color and remains white if no hemoglobin is detected. As a control, when the developer 70 flows to the second slide section 22, which is not only impregnated with guaiac but also with hemoglobin, the second slide section 22 should always turn blue if the developer 70 is functioning and the second slide section is properly impregnated. After the physician or other medical personnel view the test, the flaps 42, 44 and 54 are closed and the test card 10 is disposed.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of his invention as pertains to any apparatus not materially departing from but outside the literal scope of the invention as set out in the following claims.

What is claimed is:

1. An occult blood specimen test card for testing medical specimens comprising:

a carrier of material for inhibiting the passage of liquid therethrough;

said carrier including a central web having an opening for defining therewithin a slide section, a front side and a back side, said front side having a front flap hingably mounted thereon in covering relationship to said slide section;

said slide section having a test slide and a control slide of fluid permeable paper impregnated with a reagent mounted on a carrier;

a first ampule presenting a first frangible body and containing therewithin a quantity of developing liquid;

a first channel mounted on the carrier and including a first flexible blister enclosing therewithin said first ampule and a first tubular canal presenting a proximate open end fluidically communicating with the first blister and a remote open end positioned proximate the test slide for conveying developing liquid from the first blister to the test slide upon compression of the first blister to fracture said first ampule and expel developing liquid from the first blister through the first canal; and said first channel further including a second tubular canal presenting a proximate open end fluidically communicating with the first blister and a remote open end positioned proximate said control slide for conveying developing liquid from the first blister to said control slide upon compression of said first blister to fracture said first ampule and expel developing liquid from said first blister through said second canal.

2. A card as set forth in claim 1, said back side having a back flap hingably mounted thereon in covering relationship to said slide section.

3. A card as set forth in claim 2, wherein said slide section is positioned between said center web and said back side.

4. A card as set forth in claim 1, wherein said control slide is provided with both said reagent and a control substance for providing a chromatographic indication in the presence of the developing liquid.

5. A card as set forth in claim 1, said slide section being impregnated with guaiac and said developing solution including a solution of hydrogen peroxide.

6. A card as set forth in claim 5, wherein said carrier presents openings defining a test slide and a control slide discrete from said test slide, said first channel including a second canal having a proximate open end in fluidic communication with said first blister and a remote open end positioned in spaced relationship from said remote open end of said first canal whereby the remote open end of said first canal is positioned proximate said test slide and the remote open end of said second canal is positioned proximate said control slide.

7. A card as set forth in claim 6, including a restriction defining a check valve positioned at said proximate open end of each of said first and second canals.

8. A card as set forth in claim 1, wherein said first channel is unitary and formed of a resilient synthetic resin material.

9. A card as set forth in claim 1, wherein said frangible ampule is of glass.

10. A card as set forth in claim 1, wherein said carrier presents openings defining a test slide and a control slide discrete from said test slide, the remote open end of the first canal being positioned proximate said test slide and the remote open end of said second canal being positioned proximate said control slide.

11. A card as set forth in claim 10, including a rigid press bar positioned exteriorly of and in spanning relationship over said first and second blisters.

12. An occult blood specimen test card for detecting the presence of hemoglobin comprising:

a carrier presenting a front side, a back side and a center web positioned between said front side and said back side, said center web presenting at least one opening therein, said front side and said back side each having hingably mounted flaps thereon positioned in covering relationship to said opening;

a test slide of permeable paper impregnated with a chromatographic reagent, said test slide being positioned between said front side and said back side of said carrier and within said opening to present a first test section;

a control slide of permeable paper impregnated with a chromatographic reagent, said control slide being positioned between said front side and said back side of said carrier and within said opening to present a second test section;

a first ampule having a frangible body containing therein a quantity of a developing solution;

a first channel mounted on said carrier and including a first flexible blister defining an interior and enclosing therein said first ampule, a first canal presenting a proximate open end fluidically communicating with said interior and a remote open end positioned proximate said first test section for directing developing solution to said first test section when said first ampule is crushed within said interior to thereby cause a chromatographic reaction by said reagent in response to the presence of hemoglobin on said test slide; and a second canal presenting a proximate open end fluidically communicating with said interior and a remote open end positioned proximate said second test section for directing developing solution to said second test section when said first ampule is crushed within said interior to thereby cause a chromatoaraphic reaction by said reagent in response to the presence of hemoglobin on said control slide.

13. An occult blood specimen test card as set forth in claim 12, and including a second opening defining a second test section, a second ampule having a frangible body containing therein a quantity of developing solution, and a second channel mounted on said carrier and including a second flexible blister defining an interior and enclosing therein said second ampule and a second canal presenting a proximate open end fluidically communicating with said interior and a remote open end positioned proximate said second test section for directing developing solution to said second test section when said second ampule is crushed within said interior to thereby cause a chromatographic reaction by said reagent in response to the presence of hemoglobin on said control slide.

14. An occult blood specimen test card as set forth in claim 12, and including a second opening defining a second test section, said first channel including a second canal having a proximate open end communicating with the interior of said first blister and a remote open end proximate said second test section for directing developing solution to said second test section to thereby cause a chromatographic reaction by said reagent in response to the presence of hemoglobin on said control slide.

15. A method of testing a stool sample to determine the presence of blood therein comprising:

providing an integrated test card including a carrier, a test slide of permeable material impregnated with a chromatographic reagent and carried by the carrier, a control slide of permeable material impregnated with a chromatographic reagent and carried by the carrier, at least one ampule having a frangible body containing therein a liquid developer, a channel mounted on said carrier and including a flexible blister defining an interior in which said ampule is located, a first canal fluidically communicating said interior with said test slide, and a second canal fluidically communicating said interior with said control slide;

applying a stool sample on said test slide; and compressing said blister to crush said ampule and direct a flow of developer through said first canal to said test slide and through said second canal to said control slide for causing a chromatographic reaction on said test slide in the presence of blood on said test slide.

16. The method of claim 15, wherein said control slide is provided with both said reagent and a control substance for providing a chromatographic indication in the presence of the developing liquid.

17. The method of claim 16, further comprising the step of comparing said control slide to said test slide for determination of the presence of blood in said test slide.

18. An occult blood specimen test card for testing medical specimens comprising:

a carrier of material for inhibiting the passage of liquid therethrough;

said carrier including a central web having an opening for defining therewithin a slide section, a front side and a back side, said front side having a front flap hingably mounted thereon in covering relationship to said slide section;

said slide section having a test slide and a control slide of fluid permeable paper impregnated with a reagent mounted on a carrier;

a first ampule presenting a first frangible body and containing therewithin a quantity of developing liquid;

a second ampule presenting a second frangible body and containing therewithin a quantity of developing liquid;

a first channel mounted on the carrier and including a first flexible blister enclosing therewithin said first ampule and a first tubular canal presenting a proximate open end fluidically communicating with said first blister and a remote open end positioned proximate the test slide for conveying developing liquid from said first blister to said test slide upon compression of said first blister to fracture said first ampule and expel developing liquid from said first blister through said first canal; and a second channel mounted on said carrier discretely from said first channel and having a second flexible blister and including a second tubular canal mounted on said carrier discretely from said first channel, said second channel containing therein said second ampule having a frangible body containing a quantity of said developing liquid, said second canal fluidically communicating said second blister to said control slide.

19. A card as set forth in claim 18, said back side having a back flap hingably mounted thereon in covering relationship to said slide section.

20. A card as set forth in claim 19, wherein said slide section is positioned between said center web and said back side.

21. A card as set forth in claim 18, wherein said control slide is provided with both said reagent and a control substance for providing a chromatographic indication in the presence of the developing liquid.

22. A card as set forth in claim 18, said slide section being impregnated with guaiac and said developing liquid including a solution of hydrogen peroxide.

23. A card as set forth in claim 22, wherein said carrier presents openings defining a test slide and a control slide discrete from said test slide, said first channel including a second canal having a proximate open end in fluid communication with said first blister and a remote open end positioned in spaced relationship from said remote open end of said first canal whereby the remote open end of said first canal is positioned proximate said test slide and the remote open end of said second canal is positioned proximate said control slide.

24. A card as set forth in claim 18, wherein said first channel is unitary and formed of a resilient synthetic resin material.

25. A card as set forth in claim 18, wherein said frangible ampule is made of glass.

26. A card as set forth in claim 18, wherein said carrier presents openings defining a test slide and a control slide discrete from said test slide, the remote open end of said first canal being positioned proximate said test slide and the remote open end of said second canal being positioned proximate said control slide.

27. An occult blood specimen test card for testing medical specimens comprising:
   a carrier of material for inhibiting the passage of liquid therethrough;
   said carrier including a central web having an opening for defining therewithin a slide section, a front side and a back side, said front side having a front flap hingably mounted thereon in covering relationship to said slide section;
   said slide section having a test slide and a control slide of fluid permeable paper impregnated with a reagent mounted on a carrier;
   a first ampule presenting a first frangible body and containing therewithin a quantity of developing liquid;
   a second ampule presenting a second frangible body and containing therewithin a quantity of developing liquid;
   a first channel mounted on the carrier and including a first flexible blister enclosing therewithin said first ampule and a first tubular canal presenting a proximate open end fluidically communicating with said first blister and a remote open end positioned proximate the test slide for conveying developing liquid from said first blister to said test slide upon compression of said first blister to fracture said first ampule and expel developing liquid from said first blister through said first canal; and
   a second channel mounted on said carrier discretely from said first channel and including a second flexible blister enclosing therewithin said second ampule and a second tubular canal presenting a proximate open end fluidically communicating with said second blister and a remote open end positioned proximate said control slide for conveying developing liquid from said second blister to said control slide upon compression of said second blister to fracture said second ampule and expel developing liquid from said second blister through said second canal.

28. A card as set forth in claim 27, said back side having a back flap hingably mounted thereon in covering relationship to said slide section.

29. A card as set forth in claim 28, wherein said slide section is positioned between said center web and said back side.

30. A card as set forth in claim 28, wherein said carrier presents openings defining a test slide and a control slide discrete from said test slide, said first channel including a second canal having a proximate open end in fluidic communication with said first blister and a remote open end positioned in spaced relationship from said remote open end of said first canal whereby the remote open end of said first canal is positioned proximate said test slide and the remote open end of said second canal is positioned proximate said control slide.

31. A card as set forth in claim 27, wherein said control slide is provided with both said reagent and a control substance for providing a chromatographic indication in the presence of the developing liquid.

32. A card as set forth in claim 27, said slide section being impregnated with guaiac and said developing liquid including a solution of hydrogen peroxide.

33. A card as set forth in claim 27, wherein said first channel is unitary and formed of a resilient synthetic resin material.

34. A card as set forth in claim 27, wherein said frangible ampule is made of glass.

35. A card as set forth in claim 27, wherein said carrier presents openings defining a test slide and a control slide discrete from said test slide, the remote open end of said first canal being positioned proximate said test slide and the remote open end of said second canal being positioned proximate said control slide.

* * * * *